United States Patent [19]

Yamagishi et al.

[11] Patent Number: 4,927,979
[45] Date of Patent: May 22, 1990

[54] PROCESS FOR THE PREPARATION OF P-ETHYLPHENOL

[75] Inventors: Takanori Yamagishi, Ichihara; Tsutomu Idai, Noda; Eiji Takahashi, Chiba, all of Japan

[73] Assignee: Maruzen Petrochemical Co., Ltd., Tokyo, Japan

[21] Appl. No.: 280,692

[22] Filed: Dec. 6, 1988

[30] Foreign Application Priority Data

Dec. 18, 1987 [JP] Japan .................... 62-321002
Jun. 24, 1988 [JP] Japan .................... 63-154628

[51] Int. Cl.$^5$ .................... C07C 37/14; C07C 37/11
[52] U.S. Cl. .................... 568/791; 568/790; 568/794
[58] Field of Search .................... 568/790, 791, 794

[56] References Cited

U.S. PATENT DOCUMENTS

| | | | |
|---|---|---|---|
| 3,702,886 | 11/1972 | Argauer et al. | 423/328 |
| 3,706,807 | 12/1972 | Etherington, Jr. et al. | 568/791 |
| 3,709,979 | 1/1973 | Chu | 423/328 |
| 3,728,408 | 4/1973 | Tobias | 568/791 |
| 3,832,449 | 8/1974 | Rosinski et al. | 423/328 |
| 4,016,245 | 4/1977 | Plank et al. | 423/328 |
| 4,046,859 | 9/1977 | Plank et al. | 423/328 |
| 4,371,714 | 2/1983 | Young | 568/791 |
| 4,391,998 | 7/1983 | Wu | 568/794 |
| 4,532,368 | 7/1985 | Swanson et al. | 568/791 |

FOREIGN PATENT DOCUMENTS

| | | | |
|---|---|---|---|
| 0155331 | 9/1984 | Japan | 568/791 |
| 0155332 | 9/1984 | Japan | 568/791 |
| 0181042 | 9/1985 | Japan | 568/791 |
| 50933 | 3/1986 | Japan | |
| 352868 | 12/1972 | U.S.S.R. | 568/791 |
| 0692825 | 10/1979 | U.S.S.R. | 568/791 |

OTHER PUBLICATIONS

Catalysis by Crystalline Aluminosilicates: Characterization of Intermediate Pore-Size Zeolites by the "Constraint Index": Journal of Catalysis 67, 218-222 (1981).

Primary Examiner—Werren B. Lone
Attorney, Agent, or Firm—Frishauf, Holtz, Goodman & Woodward

[57] ABSTRACT

A very simple process for preparing p-ethylphenol is disclosed. It is only necessary to contact phenol with an ethylating agent in vapor phase in the presence of a specific catalyst. The catalyst can be obtained by incorporating one or more alkoxysilanes to a crystalline aluminosilicte with a constraint index of 1-15 having a silica/alumina molar ratio of 20-400, wherein the amount of said alkoxysilanes to be incorporated is not less than 1.4 wt % calculated as silicon based on the amount of said crystalline aluminosilicate. Because the specific catalyst has the narrowed or restricted entrances of the micro pores of the crystalline aluminosilicate by the alkoxysilane treatment, it is possible to prepare p-ethylphenol in a high selectivity. The product contains only a very small amount of m-ethylphenol. The p-ethylphenol product obtained by the process of the present invention can be employed directly as raw materials for practical uses such as synthetic resins and antioxidants without m-ethylphenol elimination procedure.

20 Claims, No Drawings

PROCESS FOR THE PREPARATION OF P-ETHYLPHENOL

BACKGROUN OF THE INVENTION

1. Field of the Invention

The present invention relates to a process for the preparation of p-ethylphenol. More particularly, the present invention relates to a process for preparing p-ethylphenol efficiently in a high selectivity, by reacting phenol and an ethylating agent such as ethylene, ethanol and the like in vapor phase in the presence of a specific catalyst. p-ethylphenol prepared by the process of the present invention has important commercial uses as intermediates for the production of synthetic resins, antioxidants and the like.

2. Description of the Prior Art

The conventional process for the preparation of p-ethylphenol comprises sulfonation of ethylbenzene, separation of p-ethylbenzenesulfonic acid by fractional crystallization from the mixture of ethylbenzenesulfonic acid isomers thus formed, and alkali fusion of p-ethylbenzenesulfonic acid. This process has long been practised industrially. Synthesis of p-ethylphenol by ethylation of phenol with an ethylating agent has been also studied. That is, proposals have been made relative to processes for ethylating phenol with an ethylating agent in vapor phase with a catalyst prepared by treatment of a crystalline aluminosilicate in a suitable manner so as to give an increased selectivity to form p-ethylphenol. For example, Japanese Patent Laid-open No. Sho 61(1986)-50933 discloses a process for the preparation of p-ethylphenol by the use of Mg, Ba or P-carrying crystalline aluminosilicate catalyst which can be obtainable by immersion of a crystalline aluminosilicate into an aqueous solution of Mg, Ba or P compound, followed by drying of the treated crystalline aluminosilicate, and then calcination in an oxygen-containing gas. U.S. Pat. No. 4,532,368 discloses a process for obtaining a mixture of m-ethylphenol and p-ethylphenol which comprises conducting ethylation of phenol by the use of a catalyst composed of a crystalline aluminosilicate carrying an oxide of a variety kinds of metals, a phosphores oxide or silica thereon, and distilling the mixture of ethylphenol isomers thus formed to remove the o-isomer. The catalyst used in the process described in U.S. Pat. No. 4,532,368 can be prepared by treatment of a crystalline aluminosilicate having a high silica content and having micro pores, the entrance of which being constituted with ten-membered ring, such as ZSM-5 zeolite developed by Mobile Oil Corp., U.S.A. defined in U.S. Pat. No. 3,702,886, with any type of various kinds of metal compounds, phosphorus compounds, silanes, or silicone compounds, followed by calcination.

SUMMARY OF THE INVENTION

In the conventional processes described above, the process for the preparation of p-ethylphenol by sulfonation of ethylbenzene followed by alkali fusion has many problems such as tedious multi-step operation, inferior operational surroundings associated with handling of dangerous high-temperature sulfuric acid and sodium hydroxide, corrosion of equipment caused by the use of sulfuric acid, and disposal of waste water containing sulfuric acid and alkali, and by-production of o- and m-ethylbenzenesulfonic acids. This process has long been used widely in industry, but for the reasons stated above, this process is not advantageous. On the other hand, the process for the preparation of a mixture of m- and p-ethylphenol isomers by ethylation of phenol is advantageous when compared to the aforementioned process via sulfonation and alkali fusion steps, because the ethylation process requires fewer steps and simpler operation, and does not cause any problems mentioned above. The process through ethylation of phenol, however, includes a serious difficulty as a process for the preparation of p-ethylphenol. That is, ethylation of phenol by the use of a conventional acidic catalyst can only give a mixture of o-, m-, and p-ethylphenol isomers. The formation of o- and m-ethylphenol isomers not only results in lowering of the yield of p-ethylphenol but also results in lowering of the purity of the p-ethylphenol product. The reason therefor is that it is difficult to separate the m-ethylphenol from the p-ethylphenol contained in the product mixture, because m-ethylphenol and p-ethylphenol have very close boiling points, and it is practically impossible to isolate p-ethylphenol from a mixture of ethylphenols by distillation. Accordingly, when an attempt is made to produce p-ethylphenol through ethylation of phenol, it is important to reduce the formation of other ethylphenol isomers, especially to reduce the formation of m-ethylphenol isomer. The process shown in Japanese Patent Laid-open No. Sho 61(1986)-50933 aforementioned intends to produce p-ethylphenol shape-selectively which has the smallest molecular-diameter within the three ethylphenol isomers by the use of a Mg, Ba or P-carrying crystalline aluminosilicate catalyst. However, the process is still insufficient as an industrial process for the preparation of p-ethylphenol in a high selectivity and in a high efficiency, because the process has still many difficulties. That is, the process can only give an ethylphenol product with p-ethylphenol content of lower than 90 wt % maximum and cannot reduce the formation of m-ethylphenol to an acceptable or permissible level, and the catalyst used in the process shows very low activity, because the micro pores of the crystalline aluminosilicate are plugged in some greater extent during the step to immerse the crystalline aluminosilicate into a solution of Mg, Ba or P-containing compounds.

Also, as stated above, the process described in U.S. Pat. No. 4,532,368 relates to a process for obtaining a mixture of m-ethylphenol and p-ethylphenol which comprises conducting ethylation of phenol by the use of a catalyst composed of a crystalline aluminosilicate carrying an oxide of a variety kinds of metals, a phosphorus oxide or silica thereon and removing o-ethylphenal from the mixture of ethylphenol isomers thus formed by distillation. The catalyst used in this process is prepared by treatment of a crystalline aluminosilicate having a high silica content and having micro pores, the entrance of which being constituted with ten-membered ring, with any type of various kinds of metal compounds, phosphorus compounds, silanes, or silicone compounds, followed by calcination. In the process, the silane or silicone compound used for the preparation of the catalyst has a molecular diameter larger than those of the entrances of the micro pores of the crystalline aluminosilicate, and therefore, silica is carried on the outside surfaces of crystals of the crystalline aluminosilicate. As the results, it is expected that the acidic points on the outside surfaces of crystals of the crystalline aluminosilicate are covered with silica, and shape-selective catalytic activity can be enhanced due to narrowing of the entrances of the micro pores of the crystalline aluminosilicate. As stated above, the object of the process described in the aforementioned U.S. patent is, however, directed to the production of a mixture containing m- and p-ethylphenol isomers, and therefore, the product obtained is a mixture of o-, m-, and p-ethylphenol isomers in which p-ethylphenol content is lower than only 30 wt %. In the process given in the aforementioned U.S. patent, by no means aims to selectively produce p-ethylphenol and the catalyst used in the process is not designed to produce selectively p-ethylphenol alone, and therefore, even employing the process, it is entirely difficult to produce p-ethylphenol in a high selectivity.

The present invention aims at solving the above-described problems associated with the conventional processes.

Accordingly, the object of the present invention is to provide a process for the preparation of useful p-ethylphenol in a high selectivity and in a high yield. The process of the present invention can provide p-ethylphenol selectively with reduced formation of o- and m-ethylphenol isomers notwithstanding by the use of a simple ethylation process of phenol with an ethylating agent.

That is, the present invention provides a process which permits a facile, high-yield, and economical production of p-ethylphenol from phenol and an ethylating agent suitable for industrial application.

Other objects of the present invention will be apparent to those in the art from the descriptions given hereunder.

We have made intensive studies toward realizing the above-described objects, and succeeded in completing the present invention by the finding that p-ethylphenol can be prepared in a high selectivity and in a high efficiency when phenol is allowed to react with an ethylating agent in vapor phase in the presence of a specific catalyst prepared by incorporating a specific alkoxysilane in a specific amount to a crystalline aluminosilicate with a constraint index of 1-15 and with a specific range of silica/alumina molar ratio.

Thus, according to the present invention, in a process for the preparation of p-ethylphenol which comprises reacting phenol with an ethylating agent in vapor phase in the presence of a catalyst, there is provided an improvement which comprises that a crystalline aluminosilicate catalyst being obtained by incorporating one or more alkoxysilanes represented by the formula $R'_nSi(OR)_{4-n}$ (wherein OR represents an alkoxy group with 1-6 carbon atoms, R' represents an alkyl group with 1-6 carbon atoms or a phenyl group and n represents an integer of 0-3) to a crystalline aluminosilicate with a constraint index of 1-15 having a silica/alumina molar ratio of 20-400, wherein the amount of said alkoxysilanes to be incorporated being not less than 1.4 wt % calculated as elemental silicon based on the amount of said crystalline aluminosilcate, is used as said catalyst.

The crystalline aluminosilicate used in the preparation of the catalyst to be employed in the process of the present invention is a crystalline aluminosilicate with a constraint index of 1-15. The term "constraint index" as used here is an index value as defined in Journal of Catalysis, 67, 218 (1981), and is represented by the ratio of cracking rates of n-hexane and 3-methylpentane during a competitive cracking reaction thereof. More specifically, an equimolar vapor mixture of n-hexane and 3-methylpentane, after diluted with five times volume of helium, is allowed to flow through a catalyst for 20 min with an LHSV of 1 hr$^{-1}$, and the molar proportions of n-hexane and 3-methylpentane remained in the product mixture are determined. The constraint index is defined by the equation described below.

$$\text{Constraint index} = \frac{\log (\text{fraction of n-hexane remaining})}{\log (\text{fraction of 3-methylpentane remaining})}$$

Incidentally, the competitive cracking reaction of n-hexane and 3-methylpentane to determine the constraint index shown above is conducted at the temperature within the range of 287°-510° C., and the temperature is so selected that the overall conversion rate is within 10-60%. With low-activity catalysts which do not allow the conversion rate to exceed 10% at a temperature below 510° C., the LHSV is lowered to raise the conversion rate to the range of 10-60%.

Relative sizes of the pores in crystalline aluminosilicates can be determined by measurements of the constraint index by the use of the aluminosilicate catalysts. That is, n-hexane has a relatively smaller molecular diameter than 3-methylpentane, and therefore, those crystalline aluminosilicates with a pore size which allows penetration of n-hexane but does not permit penetration of 3-methylpentane, show constraint indexes larger than 30. On the other hand, those crystalline aluminosilicates with a larger pore size which permits a relatively free penetration of both n-hexane and 3-methylpentane, show values smaller than 1 due to the inherent cracking reactivities of n-hexane and 3-methylpentane. An example of the former case is erionite which has an eight-membered ring at the entrance of the pore, and examples of the latter case are rare-earth element containing Y-type zeolite (REY) and H-type mordenite which have a twelve-membered ring at the entrance of the pore.

The crystalline aluminosilicates used in the present invention with a constraint index (hereinafter abbreviated occasionally as CI) of 1-15 are crystalline aluminosilicates having a medium-size pore. It is known that examples which satisfy the above requirements are ZSM-5 (CI 8.3; U.S. Pat. No. 3,702,886), ZSM-11 (CI 8.7; U.S. Pat. No. 3,709,979), ZSM-12 (CI 2.0; U.S. Pat. No. 3,832,449), ZSM-35 (CI 4.5; U.S. Pat. No. 4,016,245), and ZSM-38 (CI 2.0; U.S. Pat. No. 4,046,859), developed by Mobil Oil Corp. Preferred crystalline aluminosilicates used in the present invention are pentasil-type zeolites such as ZSM-5, ZSM-11 and the like. The CI values mentioned above are typical ones and do not strictly restricted thereto. When a crystalline aluminosilicate with constraint index outside of the range mentioned above is used, it is difficult to selectively prepare p-ethylphenol in a high yield, even if the crystalline aluminosilicate is treated with alkoxysilanes.

The crystalline aluminosilicate used as the catalyst in the process of the present invention has, as stated above, a constraint index of 1-15, and further, has a silica/alumina molar ratio of 20-400. When a crystalline aluminosilicate with a silica/alumina molar ratio outside of the range specified above is used, it is difficult to selectively prepare p-ethylphenol in a high yield, even if the crystalline aluminosilicate is treated with alkoxysilanes.

It is preferred to use a crystalline aluminosilicate having the constraint index and the silica/alumina molar ratio both specified above, and further having an average diameter of secondary crystals of 0.1-10 μm, and those having an average diameter of secondary crystals of 0.3-3 μm are especially preferred.

The crystalline aluminosilicates mentioned above contain exhangeable cations near the aluminum atoms to neutralize the electric charge. In the present invention, the catalyst is usually used in a form that the cations are firstly replaced with H+, NH4+, or polyvalent cations. It is more preferable to use the catalyst in the form that the exchangeable ions are replaced with protons (H+). As a method for converting into the H+-form, following two kinds of methods are known: (i) A method for converting directly to the H+-form by treating a crystalline aluminosilicate with a dilute aqueous solution of a mineral acid, such as hydrochloric acid, nitric acid, sulfuric acid or the like; and (ii) a method for converting indirectly to the H+-form by treating a crystalline aluminosilicate with an aqueous solution of an ammonium compound such as ammonium chloride, ammonium nitrate, ammonium sulfate or the like, and then calcining it. In the process of the present invention, it is preferable to use the H-crystalline aluminosilicate prepared by the latter method, i.e., prepared by firstly converting into the NH4+-form and then calcining it to convert into the H+-form, because the H+-crystalline aluminosilicate prepared by the indirect method shows better results when treated with alkoxysilanes, and provides p-ethylphenol in a higher selectivity and in a higher yield than the H+-crystalline aluminosilicate prepared by the former, i.e., direct method.

It is also possible to use a crystalline aluminosilicate carrying thereon one or more elements of B, P, Mn, Mg, Ca and the like, prepared by, for example, immersing a crystalline aluminosilicate into a solution containing one or more compounds of said elements; removing, if necessary, an excess amount of the solution by filtration; removing the solvent by evaporation and then drying and calcining. As the solvent, water, a lower aliphatic alcohol such as methanol, ethanol or propanol; an ether such as diethyl ether, tetrahydrofuran or dioxane; a hydrocarbon such as n-hexane, cyclohexane, benzene, toluene or xylene; and any other suitable solvents can be cited. As the compound of metals such as Mn, Mg and Ca, inorganic salts such as chlorides, nitrates or sulfates, and organic salts such as acetates or oxalates can be cited. Nitrates and acetates are preferred. As the compound of boron or phosphorus, boric acid, phosphoric acid, ammonium phosphate, diammonium hydrogen phosphate, ammonium dihydrogen phosphate, metaphosphoric acid or phosphorous pentoxide can be cited.

The crystalline aluminosilicates may be used in the powder form or after molding. They may be molded from crystalline aluminosilicates themselves or by admixture with suitable matrices. Examples of such matrices are clays, diatomaceous earths, silica, alumina, and metal oxides. The contents of such matrices in the whole catalysts should be below 90 wt % and preferably between 2-50 wt %.

The alkoxysilanes usable for the production of the crystalline aluminosilicate catalyst to be used in the process of the present invention are alkoxysilanes represented by the following formula:

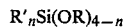

(wherein n means an integer of 0-3, OR means an alkoxy group with 1-6 carbon atoms and R' means an alkyl group with 1-6 carbon atoms or a phenyl group).

As material embodiments of the alkoxysilanes, tetramethoxysilane, tetraethoxysilane, tetrapropoxysilane, tetrabutoxysilane, methyl-trimethoxysilane, methyl-triethoxysilane, ethyl-triethoxysilane, methyl-tripropoxysilane, methyl-tributoxysilane, phenyl-trimethoxysilane, phenyl-triethoxysilane, dimethyl-dimethoxysilane, dimethyl-diethoxysilane, diethyl-diethoxysilane, diphenyl-dimethoxysilane, diphenyl-diethoxysilane, trimethyl-methoxysilane, trimethyl-ethoxysilane, triethyl-ethoxysilane and the like can be cited. Among them, it is preferred to use alkoxysilanes in which the alkoxy groups are methoxy or ethoxy group and alkyl groups are methyl or ethyl group. Especially preferred alkoxysilanes are tetramethoxysilane and tetraethoxysilane, i.e., the cases where n is 0, OR is methoxy or ethoxy group in the formula above.

In order to prepare the crystalline aluminosilicate catalyst used in the present invention, the crystalline aluminosilicate specified before is allowed to contact by a suitable manner and under a suitable condition with one or more alkoxysilanes mentioned above. By the treatment, the alkoxysilanes are carried on the crystalline aluminosilicate and the alkoxysilanes are chemically combined with the hydroxyl groups on the outer surfaces of the minute crystals of the crystalline aluminosilicate to coat the outer surfaces of the crystals. Thus, a layer of silicon compound derived from the alkoxysilane is formed depending upon the conditions employed. For the reasons stated above, the acidic points on the outer surfaces of the minute crystals of the crystalline aluminosilicate become inactive to the reaction of the present invention. Further, the entrance of the micro pores of the crystalline aluminosilicate can be narrowed or restricted by the treatment, because the layer of silicon compound thus formed overhangs to the entrances. Accordingly, it is possible to control the entrance diameter of the micro pores of the crystalline aluminosilicate by changing the amount of the alkoxysilane to be deposited. Further, since the silicon compound is an inert material and is homologous with or similar to the crystalline aluminosilicate, stable layers are formed without changing the acidic property of the crystalline aluminosilicate.

With regard to the amount of alkoxysilanes to be deposited on the crystalline aluminosilicate, in order to prepare p-ethylphenol in a high selectivity and in a high yield, it is necessary to deposit alkoxysilanes in an amount not less than 1.4 wt % calculated as elemental silicon based on the weight of the crystalline aluminosilicate. If the deposited amount is less than the value mentioned above, it is impossible to prepare p-ethylphenol selectively. Accordingly, in usual, the amount to be deposited is maintained higher than 1.4 wt % calculated as elemental silicon. On the other hand, if an amount excessively higher than the necessary level is deposited, the conversion of the reactants drops significantly, though the selectivity to p-ethylphenol becomes very high. Accordingly, preferred range is from 1.4 wt % to about 20 wt %, and more preferably 1.6 wt % to 10 wt % calculated as elemental silicon.

The treatment of the crystalline aluminosilicate with the alkoxysilanes can be performed in any suitable manner, such as in batchwise, pulsewise, or continuously by using a fixed bed or fluidized bed, and in vapor phase or liquid phase. It is also possible to conduct the treatment in one step or in multiple steps.

When conducting this treatment in vapor phase, it is possible to contact the vapor of the alkoxysilane alone with the crystalline aluminosilicate, or it is also possible to contact a vapor mixture of the alkoxysilanes and a carrier or diluent gas with the crystalline aluminosilicate. As the carrier or diluent gas, nitrogen, helium, argon, carbon dioxide, air, steam and the like can be cited. Nitrogen or helium is preferable. When carrier or diluent gas is employed, the concentration of the alkoxysilane in the vapor mixture is not necessarily limited, but in usual cases, a concentration of not less than 0.1 vol % is suitable. Treating temperature can usually be selected within a range of 10°–500° C., and preferably within a range of 150°–350° C. Treating pressure is not restricted, if the alkoxysilanes can be kept in vapor phase.

When conducting this treatment in liquid phase, it is possible to contact a liquid alkoxysilane per se with the crystalline aluminosilicate, or it is also possible to contact a solution of an alkoxysilane in a suitable solvent with the crystalline aluminosilicate. As the solvent, organic solvents such as aromatic hydrocarbons like benzene, toluene or xylenes; lower paraffinic hydrocarbons like pentane, hexane, heptane or octane; lower alcohols like methanol, ethanol or propanol, or a mixture of such alcohol and water in which water content is less than 30 wt %; and the like can be cited. When solvent is used, the concentration of the alkoxysilanes in the solution is not necessarily limited, but in general, it is suitable to use a concentration of higher than 0.1 wt %. Treating temperature is not limited, if the treating liquid, i.e., the alkoxysilane or a solution thereof, can be kept in liquid phase. In general, however, it is suitable to use a temperature of 10°–150° C. After completion of the treatment, the treating liquid is removed by filtration or evaporation.

The crystalline aluminosilicate carrying thereon the alkoxysilane in an amount of not less than 1.4 wt % calculated as elemental silicon thus prepared by the procedures mentioned above can directly be used as the catalyst for the reaction of the present invention, or if necessary or desired, can be used, after a post treatment or post treatments, as the catalyst for the reaction of the present invention. As the post treatment, any one of conventional treatment widely used in the preparation of usual catalysts such as washing, drying, calcining and the like can be cited. Among these treatments, it is possible to use only one treatment or to conduct multiple kinds of treatments. Usually, washing is carried out by using water or organic solvents such as aromatic hydrocarbons like benzene, toluene or xylene; lower paraffinic hydrocarbons like pentane, hexane, heptane or octane; and lower alcohols like methanol, ethanol or propanol. Usually, drying is carried out by contacting the catalyst with helium, nitrogen, argon, carbon dioxide, air or the like, or by maintaining the catalyst under a reduced pressure or vacuum wherein the temperature is not necessarily limited, but usually, it is suitable to use a temperature of 10°–200° C. Usually, calcination is carried out under helium, nitrogen, argon, air, steam or the like, or under a reduced pressure or vacuum. Especially, it is preferred to conduct calcination in an oxygen containing gas such as air. It is suitable to use a calcination temperature of 300°–700° C. and more preferable range is 400°–600° C.

In the crystalline aluminosilicate catalyst to be used in the process of the present invention, the form or type of the deposition of the alkoxysilane to be deposited on the crystalline aluminosilicate is not necessarily limited, and various forms or types of deposition may be appeared depending upon the catalyst preparation conditions used, and any one of such types of depositions is acceptable.

The ethylation of phenol in accordance with the process of the present invention can be carried out by contacting, in vapor phase, a gaseous mixture of phenol and an ethylating agent with the crystalline aluminosilicate catalyst mentioned above, i.e., the catalyst prepared by conducting a treatment to incorporate the alkoxysilane to the crystalline aluminosilicate, and further, if necessary, conducting one or more post treatments. As the ethylating agent used in the process of the present invention, ethanol, ethylene, acetaldehyde, ethyl chloride and the like can be cited, in which ethanol and ethylene are especially preferred. As the reaction system, a batchwise operation, a fixed-bed or fluidized-bed continuous operation and the like can be adopted, in which adoptation of a fixed-bed or fluidized-bed continuous operation is especially preferred. It is also possible to conduct the reaction by diluting the gaseous reaction mixture of phenol and an ethylating agent with a diluent such as helium, nitrogen, carbon dioxide, benzene, steam and the like.

When ethylene is used as the ethylating agent, steam is especially preferred as the diluent, because steam acts as a reaction promotor and is helpful to increase the yield of p-ethylphenol. It is preferred to use a reaction feed with water/phenol molar ratio of 0.05–50, and more preferably 0.2–12. When ethanol is used as the ethylating agent, in general, the addition of steam is unnecessary, because steam is automatically generated by the ethylation reaction, but it is also possible, of course, to introduce additional steam into the reaction system, if it is desired to do so. In this case, too, the amount of steam is selected from the range just mentioned above.

It is necessary to keep the reation temperature not lower than 200° C. so as to keep the reaction feed in vapor phase. On the other hand, if the reaction temperature reaches to a high temperature of over 600° C., a problem occurs relative to the selectivity to p-ethylphenol. Accordingly, the reaction temperature should be kept within a range of 200°–600° C. In general, a temperature of 300°–550° C. is selected as the preferred reation temperature. The reaction pressure is not necessarily limited, if the reaction feed can be kept in vapor phase. In general, however, it is preferred to use a pressure of not higher than 10 $Kg/cm^2 \cdot G$.

The reaction can be carried out by using a reaction feed with molar ratio of phenol relative to the ethylating agent (phenol/ethylating agent) within a range of 0.1–20, but preferably within a range of 0.2–5.

When conducting the ethylation reaction in a continuous manner by the use of a fixed-bed reaction system, the reaction may be performed in a weight hourly space velocity (WHSV) of 0.2–160 $hr^{-1}$, and more preferably 0.4–40 $hr^{-1}$. Incidentally, the WHSV mentioned above is calculated on the basis of total feed, i.e., sum of phenol and the ethylating agent. When the reaction condition is expressed in another way, the ratio of weights (g) of the catalyst/moles of feed (phenol, the ethylating agent and steam) to be charged in one hour (W/F) is 0.2–200 $g \cdot hr \cdot mol^{-1}$, and preferably 0.8–100 $g \cdot hr \cdot mol^{-1}$. The value W/F has a direct correlationship with the contact time of the reactants with the catalyst.

In accordance with the process of the present invention, even by the use of a process for ethylation of phenol which is a relatively simple operation, it is possible to produce inductrially useful p-ethylphenol in a high selectivity and yield when compared to conventional processes by depressing the formation of o-ethylphenol, and m-ethylphenol which is a material very difficult to separate from p-ethylphenol.

It is a truely, extraordinarily unexpected finding that as shown hereinbefore in detail and as shown in examples given hereunder, when specific catalyst prepared by incorporating a specific alkoxysilane in a specific amount to a crystalline aluminosilicate with a specific constraint index and specific composition is used, an ethylphenol product with p-ethylphenol content of 79–95.9%, in almost higher than 90%, can be obtained, as materially shown in the following examples. It will be more apparent when compared to the results obtained in U.S. Pat. No. 4,532,368 that the fact mentioned above is an extraordinarily unexpected results. In the process shown in the U.S. patent just mentioned above, it is only possible to produce a mixture of ethylphenol isomers with p-ethylphenol content of lower than only 30%.

DESCRIPTION OF THE PREFERRED EMBODIMENT

The present invention will be illustrated materially by way of examples, but these examples are only given for illustration purposes and should not be construed as limiting the present invention.

EXAMPLE 1

This example is not within the scope of the present invention, and is given for comparison purpose.

Na-ZSM-5 was prepared according to U.S. Pat. No. 3,702,886 by feeding raw materials with silica/alumina molar ratio of 100. The Na-ZSM-5 thus obtained had a silica/alumina molar ratio of 96 as determined by X-ray fluorescence analysis, and had an average diameter of the secondary crystals of 1.4 $\mu$m as determined by electron microscope. This Na-ZSM-5 (70 g) was soaked in 500 ml of 1N aqueous ammonium nitrate, refluxed for 12 hr, cooled and kept as it stands, and then the supernatant solution was removed by decantation. The addition of 500 ml of 1N aqueous nitrate, reflux, and decantation described above were repeated three more times, and the solid was washed with water and dried overnight at 120° C. to produce $NH_4$-ZSM-5. The $NH_4$-ZSM-5 thus produced was calcined in an air stream at 540° C. for 6 hr to produce H-ZSM-5.

The H-ZSM-5 thus obtained was crushed and the 16–28 mesh fraction was separated and recovered as H-ZSM-5 catalyst. A part of the 16–28 mesh fraction was packed in a quartz reaction tube, and phenol was ethylated with ethylene by a fixed-bed flow system. The reaction conditions were as follows:

| Amount of the catalyst | 2.0 g |
| --- | --- |
| Phenol/ethylene/steam molar ratio | 1.0/0.86/1.3 |
| Catalyst weight/one mole of total feed, i.e., sum of phenol, ethylene and steam, per hour (W/F) | 3.5 g · hr · mol$^{-1}$ |
| WHSV (steam exclusive) | 10.7 hr$^{-1}$ |
| Pressure | Atmospheric pressure |
| Temperature | 400° C. |

Analysis of the reaction product (by gas chromatography) after 2 hr from the start of the reaction gave the results shown in Table 1.

EXAMPLE 2

Four (4.0) g of the 16–28 mesh fraction of H-ZSM-5 obtained in Example 1 was packed in a glass reaction tube and was dehydrated at 450° C. for 1.5 hr in a helium gas stream. Then, the H-ZSM-5 was contacted with a helium gas stream containing 1 vol % of tetramethoxysilane at 200° C. for 30 hr in a fixed-bed flow type reactor by passing the mixed gas of helium and tetramethoxysilane in a flow rate of 1.0 l/min. Thereafter, calcination was conducted in an air stream at 450° C. for 1 hr and at 540° C. for 10 hr.

The deposited amount of the silicon compound derived from alkoxysilane used, (hereinafter simply referred to "silicon compound"), was measured by X-ray fluorescence analysis and found that the deposited amount was 7.4 wt % calculated as elemental silicon based on the amount of the crystalline aluminosilicate, i.e., H-ZSM-5.

The catalyst thus obtained (2.0 g) was packed in a quartz reaction tube and ethylation of phenol with ethylene was conducted in the same manner and under the same conditions as used in Example 1. The analytical results of the product obtained after 2 hr from the start of the reaction are shown in Table 1.

EXAMPLE 3

A 16–28 mesh fraction of H-ZSM-5 was prepared in the same manner and under the same conditions as described in Example 1 from the Na-ZSM-5 obtained in Example 1. Two (2.0) g of the 16–28 mesh fraction of H-ZSM-5 thus obtained was packed in a quartz reaction tube, and a treatment with tetramethoxysilane was conducted in the same conditions as used in Example 2 except that after the treatment with tetramethoxysilane, calcination in an air stream was not conducted, but a helium gas stream was passed for 30 min at the treatment temperature, i.e., 200° C.

Then, by using the catalyst instantly obtained per se, i.e., without subjecting any further treatment, ethylation of phenol with ethylene was conducted in the same manner and under the same conditions as used in Example 1. The analytical results of the product obtained after 2 hr from the start of the reaction are shown in Table 1.

EXAMPLE 4

Four (4.0) g of the 16–28 mesh fraction of H-ZSM-5 obtained in Example 1 was packed in a glass tube sealed at one end, and dehydration was carried out under vacuum by evacuation at 450° C. for 2 hr. Then, after lowering the temperature of H-ZSM-5 bed to 320° C., 4.0 g of tetramethoxysilane kept at room temperature was introduced into the system and evolved tetramethoxysilane vapor was contacted with the H-ZSM-5. The system was kept as it stands for 1 week and then the system was vented longer than 30 min. Thereafter, calcination was conducted in an air stream at 450° C. for 1 hr and at 540° C. for 10 hr.

All of the above steps were repeated once more. The amount of the silicon compound deposited was measured by X-ray fluorescence analysis and found as 7.9 wt % calculated as elemental silicon.

The catalyst (2.0 g) was packed in a quartz reaction tube, and ethylation of phenol with ethylene was conducted in the same manner and under the same conditions as used in Example 1. The analytical results of the product obtained after 2 hr from the start of the reaction are shown in Table 1.

EXAMPLE 5

Eight (8.0) g of the 16–28 mesh fraction of H-ZSM-5 obtained in Example 1 was put into a flask and dehydration was conducted by keeping the flask in a drier kept at 120° C. for 10 hr. Then, a solution comprising 100 g of toluene and 8.0 g of tetramethoxysilane was poured into the flask and the contents were refluxed at 90° C. for 15 hr. Thereafter, the solution was filtered off and the solid material was air dried and calcined in an air stream at 200° C. for 2 hr and at 540° C. for 12 hr.

The amount of the silicon compound deposited on the catalyst was measured by X-ray fluorescence analysis and was found as 2.1 wt % calculated as elemental silicon.

The catalyst (2.0 g) was packed in a quartz reaction tube, and ethylation of phenol with ethylene was conducted in the same manner and under the same conditions as used in Example 1. The analytical results of the product obtained after 2 hr from the start of the reaction are shown in Table 1.

EXAMPLE 6

Two (2.0) g of the catalyst prepared in Example 5 was packed into a quartz reaction tube, and ethylation of phenol with ethanol was conducted continuously in the fixed-bed reactor. Reaction conditions were as follows:

| | |
|---|---|
| Amount of the catalyst | 2.0 g |
| Phenol/ethanol molar ratio | 1.0/0.86 |
| W/F | $3.5 \text{ g} \cdot \text{hr} \cdot \text{mol}^{-1}$ |
| WHSV | $20.0 \text{ hr}^{-1}$ |
| Pressure | Atmospheric pressure |
| Temperature | 400° C. |

Incidentally, calculation basis of the amount of feed (F) is the sum of phenol and ethanol. The analytical results of the product obtained after 2 hr from the start of the reaction are as shown in Table 1.

EXAMPLE 7

Eight (8.0) g of the 16–28 mesh fraction of H-ZSM-5 obtained in Example 3 was put into a flask and dehydration was conducted by keeping the flask in a drier kept at 120° C. for 10 hr. Then, a solution comprising 200 g of toluene and 8.0 g of tetramethoxysilane was poured into the flask and the contents were refluxed at 90° C. for 15 hr. Thereafter, the solution was filtered off and the solid material was air-dried overnight at room temperature.

The amount of the silicon compound deposited on the catalyst was measured by X-ray fluorescence analysis and found as 2.4 wt % calculated as elemental silicon.

The catalyst (2.0 g) was packed into a quartz reaction tube, and ethylation of phenol with ethylene was conducted in the same manner and under the same conditions as used in Example 1. The analytical results of the product obtained after 2 hr from the start of the reaction are shown in Table 1.

EXAMPLE 8

Two (2.0) g of the catalyst prepared in Example 7 was packed in a quartz reaction tube, and ethylation of phenol with ethanol was carried out in the same manner and under the same conditions as used in Example 6. The analytical results of the product obtained after 2 hr from the start of the reaction are shown in Table 1.

EXAMPLE 9

Eight (8.0) g of the 16–28 mesh fraction of H-ZSM-5 obtained in Example 3 was put into a flask and dehydration was conducted by keeping the flask in a drier kept at 120° C. for 10 hr. A solution comprising 200 g of toluene and 11.0 g of tetraethoxysilane was poured into the flask and the contents were refluxed for 24 hr at 90° C. Thereafter, the solution was filtered off and the solid material was air-dried overnight at room temperature.

The amount of the silicon compound deposited on the catalyst thus obtained was measured by X-ray fluorescence analysis and found as 2.0 wt % calculated as elemental silicon.

The castalyst (2.0 g) was packed into a quartz reaction tube, and ethylation of phenol with ethylene was conducted in the same manner and under the same conditions as used in Example 1. The analytical results of the product obtained after 2 hr from the start of the reaction are shown in Table 1.

EXAMPLE 10

Four (4.0) g of the catalyst prepared in Example 9 was calcined in an air stream at 200° C. for 2 hr and at 540° C. for 12 hr.

The catalyst (2.0 g) was packed in a quartz reaction tube, and ethylation of phenol with ethylene was conducted in the same manner and under the same conditions as used in Example 1. The analytical results of the product obtained after 2 hr from the start of the reaction are shown in Table 1.

EXAMPLE 11

This example is not within the scope of this invention, and is given only for comparative purpose.

Eight (8.0) g of the 16–28 mesh fraction of H-ZSM-5 obtained in Example 1 was put into a flask and dehydration was conducted by keeping the flask in a drier kept at 120° C. for 12 hr. Then, a solution comprising 200 g of toluene and 8.0 g of tetramethoxysilane was poured into the flask and the contents were refluxed at 90° C. for 6 hr. Then, the solution was filtered off and solid material was air-dried. Thereafter, calcination was conducted in an air stream at 200° C. for 2 hr and at 540° C. for 12 hr.

The amount of silicon compound deposited on the catalyst thus obtained was measured by X-ray fluorescence analysis and found as 1.1 wt % calculated as elemental silicon.

The catalyst (2.0 g) was packed in a quartz reaction tube and ethylation of phenol with ethylene was conducted in the same manner and under the same conditions as used in Example 1. The analytical results of the product obtained after 2 hr from the start of the reaction are shown in Table 1.

EXAMPLE 12

Two (2.0) g of the catalyst obtained in Example 11 was packed in a glass reaction tube and dehydration was conducted by passing a helium gas stream at 450° C. for 1.5 hr. Thereafter, a helium gas stream containing 26 vol % of trimethylmethoxysilane was contacted with the catalyst in a flow rate of 0.64 l/min at 320° C. for 1 hr in a fixed-bed flow system. Thereafter, calcination was conducted in an air stream at 450° C. for 1 hr and at 540° C. for 10 hr.

The amount of the silicon compound deposited on the catalyst thus obtained was measured by X-ray fluorescence analysis and found as 2.6 wt % calculated as elemental silicon.

Incidentally, the value 2.6 wt % was the total deposition formed during the procedures given in Example 11 and this Example, and the deposition newly formed during the procedure of this Example was 1.5 wt %.

The catalyst (2.0 g) was packed in a quartz reaction tube, and ethylation of phenol with ethylene was conducted in the same manner and under the same conditions as used in Example 1. The analytical results of the product obtained after 2 hr from the start of the reaction are shown in Table 1.

EXAMPLE 13

Two (2.0) g of the catalyst obtained in Example 11 was packed in a glass reaction tube and dehydration was conducted in a helium gas stream at 450° C. for 1.5 hr. Then, a helium gas mixture containing 9.0 vol % of dimethyldimethoxysilane was contacted with the catalyst in a flow rate of 0.64 l/min at 300° C. for 15 min in a fixed-bed flow system. Thereafter, calcination was conducted in an air stream at 450° C. for 1 hr and at 540° C. for 10 hr.

The amount of the silicon compound deposited on the catalyst thus obtained was measured by X-ray fluorescence analysis and found as 2.4 wt % calculated as elemental silicon (the amount already deposited in Example 11 inclusive).

The catalyst (2.0 g) was packed in a quartz reaction tube, and ethylation of phenol with ethylene was conducted in the same manner and under the same conditions as used in Example 1. The analytical results of the product obtained after 2 hr from the start of the reaction are shown in Table 1.

EXAMPLE 14

Four (4.0) g of the 16–28 mesh fraction of H-ZSM-5 obtained in Example 3 was put into a flask and the flask was kept in a desiccator containing a saturated aqueous solution of ammonium chloride as a dehydrating agent overnight. Then, a solution comprising 100 g of toluene and 4.0 g of tetramethoxysilane was poured into the flask and the contents were refluxed at 90° C. for 1.5 hr. Then, the solution was filtered off and the solid material was air-dried. The solid material was calcined in an air stream at 200° C. for 2 hr and at 540° C. for 12 hr.

The amount of the silicon compound deposited on the catalyst thus obtained was measured by X-ray fluorescence analysis and found as 2.7 wt % calculated as elemental silicon.

The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 15

To the H-ZSM-5 obtained in Example 1, an alumina sol was added in an amount to provide an alumina binder content of 5.0 wt % and they were mixed well. Then, the mixture was air-dried overnight and dried at 120° C. for 4 hr. Thereafter, the mixture was crushed and the 16–28 mesh fraction was separated and recovered. The fraction was calcined in an air stream at 400° C. for 2 hr and at 540° C. for 12 hr to produce H-ZSM-5/Al$_2$O$_3$. Four (4.0) g of H-ZSM-5/Al$_2$O$_3$ thus obtained was put into a flask and dehydration was conducted by keeping the flask in a drier kept at 120° C. for 10 hr. Then, a solution comprising 100 g of toluene and 4.0 g of tetramethoxysilane was poured into the flask and the contents of the flask were refluxed at 90° C. for 24 hr. Thereafter, the solution was filtered off and the solid material was air-dried. The solid material was calcined in an air stream at 200° C. for 2 hr and at 540° C. for 12 hr.

The amount of the silicon compound deposited on the catalyst was measured by X-ray fluorescence analysis and found as 2.5 wt % calculated as elemental silicon.

The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 16

This example is not within the scope of the present invention, and is given for comparative purpose.

A 16–28 mesh fraction of H-ZSM-5 was prepared in the same manner and under the same conditions as described in Example 1 from the Na-ZSM-5 obtained in Example 1. Eight and half (8.5) g of the 16–28 mesh fraction of H-ZSM-5 thus obtained was put into a flask and a solution composed of 100 g of n-hexane and 1.1 g of tetramethoxysilane was poured into the flask. The contents of the flask were refluxed for 1 hr at 65° C. Then, the solution was filtered off and the solid material was air-dried. Thereafter, the solid material was calcined in an air stream at 200° C. for 2 hr and at 540° C. for 12 hr.

The amount of the silicon compound deposited on the catalyst was measured by X-ray fluorescence analysis and found as 0.9 wt % calculated as elemental silicon.

The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 17

This example is not within the scope of the present invention, and is given for comparison purpose.

Na-ZSM-5 was prepared by feeding raw materials with a silica/alumina molar ratio of 300 according to U.S. Pat. No. 3,702,886. The Na-ZSM-5 thus obtained had a silica/alumina molar ratio of 285 as determined by X-ray fluorescence analysis, and had an average diameter of the secondary crystals of 1.6 μm as determined by electron microscope. The Na-ZSM-5 (70 g) was treated in the same manner and under the same conditions as used in Example 1 to produce H-ZSM-5.

The H-ZSM-5 thus obtained was crushed and the 16–28 mesh fraction was separated and recovered as H-ZSM-5 catalyst. The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 18

A catalyst carrying silicon compound was prepared by treating and calcining the H-ZSM-5 catalyst obtained in Example 17 in the same manner and under the same conditions as used in Example 5. The amount of silicon compound deposited on the catalyst was measured by X-ray fluorescence analysis and found as 1.9 wt % calculated as elemental silicon. The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 19

This example is not within the scope of the present invention, and is given only for the comparison purpose.

Na-ZSM-5 was prepared by feeding raw materials with a silica/alumina molar ratio of 500 according to U.S. Pat. No. 3,702,886. The Na-ZSM-5 thus obtained had a silica/alumina molar ratio of 478 as determined by X-ray fluorescence analysis, and had an average diameter of the secondary crystals of 1.6 $\mu$m as determined by electron microscope. The Na-ZSM-5 (70 g) was treated in the same manner and under the same conditions as used in Example 1 to produce H-ZSM-5.

The H-ZSM-5 thus obtained was crushed and the 16–28 mesh fraction was separated and recovered as H-ZSM-5 catalyst. The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 20

This example is not within the scope of the present invention, and is given only for the comparison purpose.

A catalyst carrying silicon compound was prepared by treating and calcining the H-ZSM-5 catalyst obtained in Example 19 in the same manner and under the same conditions as used in Example 5. The amount of the silicon compound deposited on the catalyst was measured by X-ray fluorescence analysis and found as 1.6 wt % calculated as elemental silicon. The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 21

This example is not within the scope of the present invention, and is given only for the comparison purpose.

Thirty (30) g of Na-ZSM-5 synthesized in Example 1 was immersed into 500 ml of 0.6N aqueous solution of hydrochloric acid at room temperature for 24 hr under agitation with a magnetic stirrer. Then, the mixture was kept as it stands and the supernatant was removed by decantation. The addition of 500 ml of 0.6N aqueous solution of hydrochloric acid, agitation and decantation were repeated three more times, and then solid material was washed with pure water until chlorine ion could not be detected. Then, the solid material was dried at 120° C. for 12 hr to produce H-ZSM-5.

The H-ZSM-5 was crushed and the 16–28 mesh fraction was separated and recovered as H-ZSM-5 catalyst. The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 22

A catalyst carrying silicon compound was prepared by treating and calcining the H-ZSM-5 catalyst obtained in Example 21 in the same manner and under the same conditions as used in Example 5. The amount of the silicon compound deposited on the catalyst was measured by X-ray fluorescence analysis and found as 2.0 wt % calculated as elemental silicon. The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 23

This example is not within the scope of the present invention, and is given only for the comparison purpose.

Na-ZSM-11 was prepared by feeding raw materials with a silica/alumina molar ratio of 70 according to U.S. Pat. No. 3,709,979. The Na-ZSM-11 thus obtained had a silica/alumina molar ratio of 68 as determined by X-ray fluorescence analysis, and had an average diameter of the secondary crystals of 1.8 $\mu$m as determined by electron microscope. As in the case of Example 1, the Na-ZSM-11 (70 g) was converted into NH$_4$-ZSM-11 by ion-exchange, and then NH$_4$-ZSM-11 was calcined to produce H-ZSM-11.

The H-ZSM-11 thus obtained was crushed and the 16–28 mesh fraction was separated and recovered as H-ZSM-11 catalyst. The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

EXAMPLE 24

Four (4.0) g of the 16–28 mesh fraction of H-ZSM-11 obtained in Example 23 was put into a flask and dehydration was conducted by keeping the flask in a drier kept at 120° C. for 12 hr. A solution composed of 100 g of toluene and 4.0 g of tetramethoxysilane was poured into the flask. The contents of the flask were refluxed for 30 hr at 90° C. Then, the solution was filtered off, and the solid material was dried and calcined in an air stream at 200° C. for 2 hr and at 540° C. for 12 hr.

The amount of the silicon compound deposited on the catalyst was measured by X-ray fluorescence analysis and found as 2.8 wt % calculated as elemental silicon.

The catalyst (2.0 g) was packed in a quartz reaction tube, and ethylation of phenol with ethylene was conducted in the same manner and under the same conditions as used in Example 1. The analytical results of the reaction product obtained after 2 hr from the start of the reaction are shown in Table 1.

TABLE 1

| Example No. | Conversion of phenol (mol %) | Selectivity to EP* (mol %) | Composition of EP* (%) | | |
|---|---|---|---|---|---|
| | | | p- | m- | o- |
| 1** | 42.0 | 83 | 17.3 | 51.9 | 30.8 |
| 2 | 8.9 | 90 | 94.4 | 4.5 | 1.1 |
| 3 | 6.5 | 91 | 95.7 | 3.6 | 0.7 |
| 4 | 7.2 | 91 | 95.9 | 3.4 | 0.7 |
| 5 | 9.8 | 90 | 93.0 | 5.7 | 1.3 |
| 6 | 7.9 | 89 | 94.3 | 4.3 | 1.4 |
| 7 | 6.6 | 91 | 95.1 | 4.0 | 0.9 |
| 8 | 5.8 | 90 | 95.5 | 3.6 | 0.9 |
| 9 | 8.5 | 91 | 93.9 | 4.9 | 1.2 |
| 10 | 10.8 | 90 | 92.5 | 6.0 | 1.5 |
| 11** | 19.4 | 86 | 64.6 | 29.4 | 6.0 |
| 12 | 10.5 | 92 | 94.0 | 5.0 | 1.0 |
| 13 | 12.0 | 89 | 91.4 | 6.9 | 1.7 |
| 14 | 8.2 | 91 | 94.6 | 4.5 | 0.9 |
| 15 | 10.4 | 90 | 91.0 | 7.0 | 2.0 |
| 16** | 19.6 | 86 | 43.0 | 46.4 | 10.6 |
| 17** | 37.0 | 85 | 17.9 | 51.7 | 30.4 |
| 18 | 9.1 | 90 | 90.9 | 7.2 | 1.9 |
| 19** | 23.2 | 86 | 18.0 | 49.6 | 32.4 |
| 20** | 5.2 | 89 | 81.0 | 15.9 | 3.1 |
| 21** | 33.9 | 83 | 19.2 | 52.4 | 28.4 |
| 22 | 10.3 | 89 | 79.0 | 17.3 | 3.7 |
| 23** | 41.2 | 81 | 17.5 | 51.8 | 30.7 |
| 24 | 9.3 | 89 | 90.4 | 7.7 | 1.9 |

*EP means ethylphenols.
**Examples given for comparative purpose.

What is claimed is:

1. In a process for the preparation of a mixture of ethylphenol isomers which comprises reacting phenol with an ethylating agent selected from the group consisting of ethylene and ethanol in the vapor phase in the presence of a catalyst at a temperature of 200°–600° C. under a pressure of not higher than 10 Kg/cm$^2$.G, the improvement which comprises that said mixture of ethylphenol isomers has a p-ethylphenol content of higher than about 80 wt. % and said catalyst comprises a crystalline aluminosilicate catalyst obtained by incorporating one or more alkoxysilanes represented by the formula R'$_n$Si(OR)$_{4-n}$ wherein OR represents an alkoxy group having 1-6 carbon atoms, R' represents an alkyl group having 1-6 carbon atoms or a phenyl group and n represents an integer of 0-3, on a crystalline aluminosilicate having a constraint index of 1-15 and a silica/alumina molar ratio of 20-400, the amount of said incorporated alkoxysilanes being not less than 1.4 wt. % calculated as elemental silicon based on the amount of said crystalline aluminosilicate.

2. The process according to claim 1, wherein said crystalline aluminosilicate is a zeolite selected from the group consisting of ZSM-5, ZSM-11, ZSM-12, ZSM-35 and ZSM-38.

3. The process according to claim 1, wherein said crystalline aluminosilicate is a pentasil-type zeolite.

4. The process according to claim 3, wherein said pentasil-type zeolite is ZSM-5 or ZSM-11.

5. The process according to claim 1, wherein said crystalline aluminosilicate is an H-crystalline aluminosilicate.

6. The process according to claim 5, wherein said H-crystalline aluminosilicate is obtained by treating a crystalline aluminosilicate with an aqueous solution of one or more ammonium salts and then calcining thereby converting exchangeable cations positioned near the aluminum atoms into H+ ions.

7. The process according to claim 1, wherein said alkoxy group of said alkoxysilane is a methoxy group or an ethoxy group and said alkyl group of said alkoxysilane is a methyl group or an ethyl group.

8. The process according to claim 1, wherein the weight hourly space velocity (WHSV) calculated in the total of said phenol and said ethylating agent is 0.2-160 hr$^{-1}$.

9. The process according to claim 1, wherein said catalyst is prepared by calcining after the incorporation of said alkoxysilanes.

10. The process according to claim 1, wherein said catalyst is prepared without calcination after the incorporation of said alkoxysilanes.

11. The process according to claim 1, wherein the molar ratio of said phenol to said ethylating agent (phenol/ethylating agent) is 0.1-20.

12. The process according to claim 1, wherein said phenol and said ethylating agent are reacted in the presence of steam.

13. The process according to claim 12, wherein the molar ratio of said steam to said phenol (steam/phenol) is 0.05-50.

14. The process according to claim 13, wherein the ethylating agent is ethylene and the molar ratio of phenol to ethylene (phenol/ethylene) is 0.1-20.

15. The process according to claim 11, wherein said ethylating agent is ethanol.

16. The process according to claim 4, wherein said crystalline aluminosilicate is an H-crystalline aluminosilicate and in the ethylating reaction the weight hourly space velocity is 0.2-160 hr$^{-1}$ and a molar ratio of said phenol to said ethylating agent (phenol/ethylating agent) is 0.1-20.

17. The process according to claim 16, wherein said H-crystalline aluminosilicate is obtained by treating a crystalline aluminosilicate with an aqueous solution of one or more ammonium salts and then calcining thereby converting exchangeable cations positioned near the aluminum atoms into H+ ions.

18. The process according to claim 17, wherein said alkoxysilane is tetramethoxysilane or tetraethoxysilane.

19. The process according to claim 18, wherein said ethylating agent is ethylene and said ethylating reaction is conducted in the presence of steam in an amount of 0.05-50 moles per 1 mole of phenol.

20. The process according to claim 1, wherein the p-ethylphenol content of said mixture of ethylphenol isomers is in excess of 90%.

* * * * *